Figure 1:
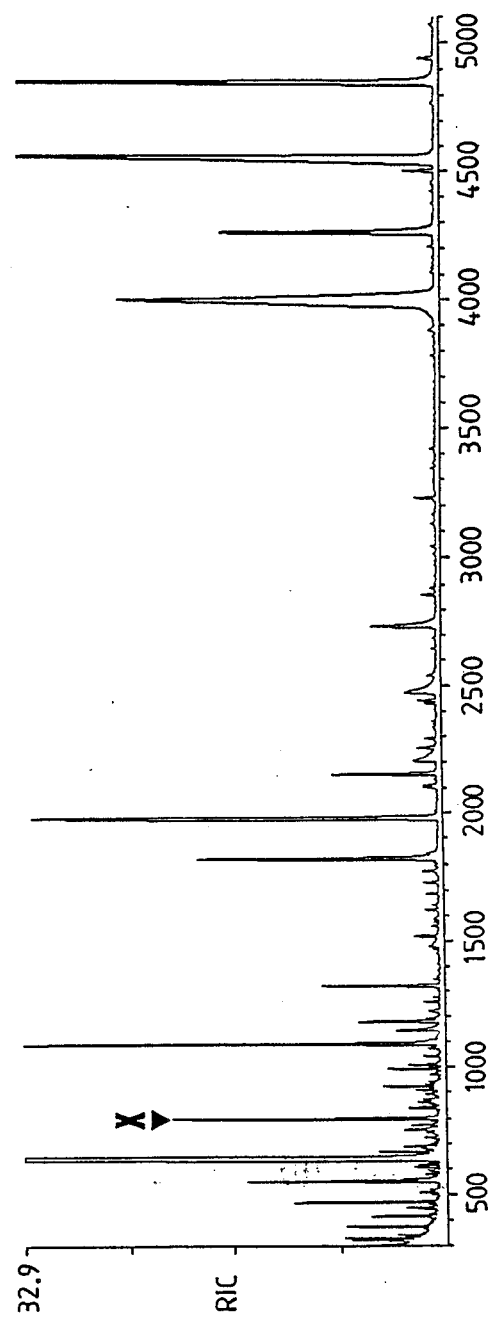
Figure 2:
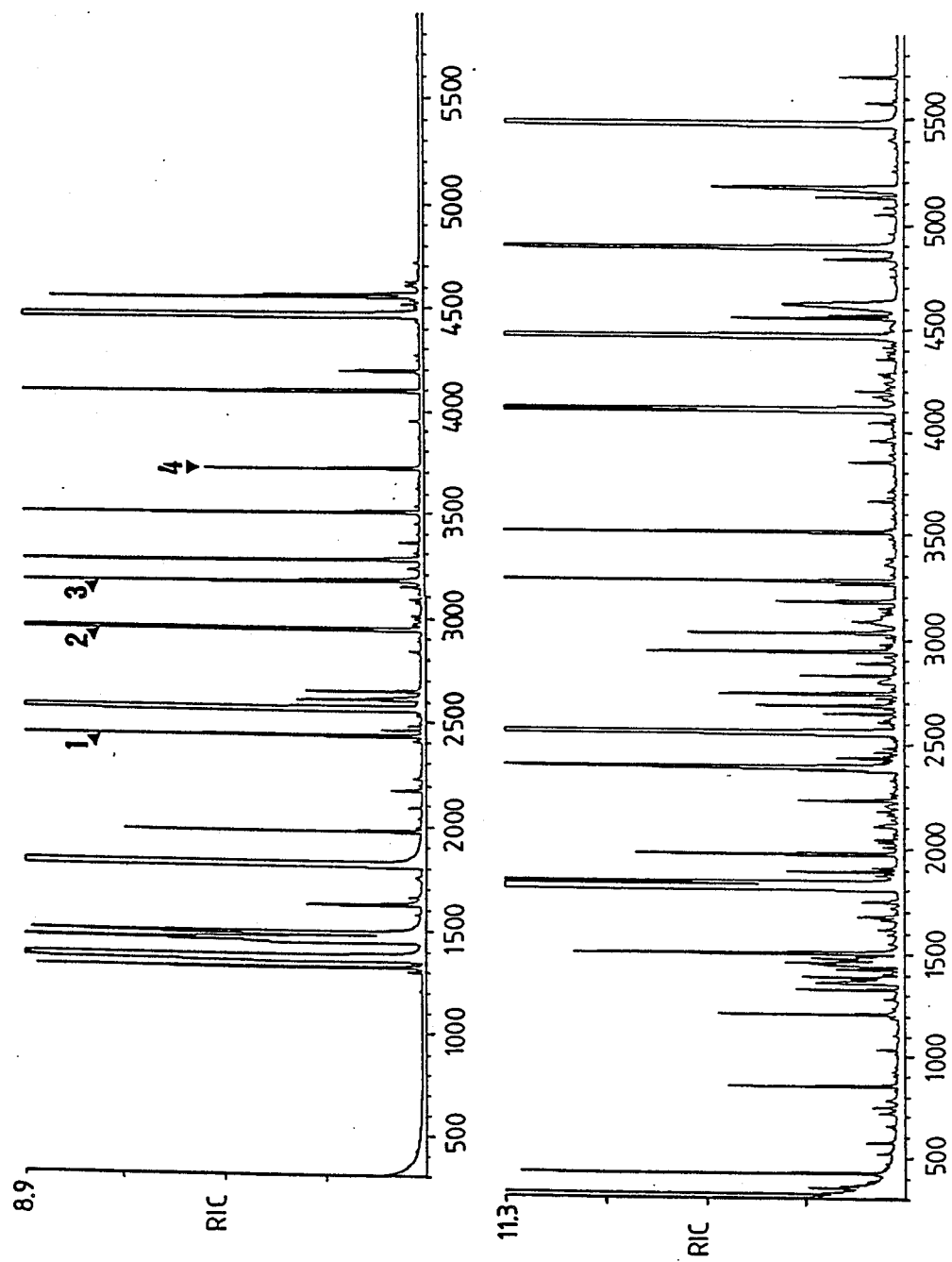

United States Patent [19]
Joulain et al.

[11] Patent Number: 4,840,792
[45] Date of Patent: Jun. 20, 1989

[54] AGENT NEUTRALIZING BAD SMELLS FROM EXCRETIONS AND EXCREMENTS OF ANIMALS

[75] Inventors: Daniel Joulain, Grasse; Philippe Racine, Chateauneuf de Grasse; Françoise Maire, Neuilly sur Seine, all of France

[73] Assignee: Robertet S.A., Grasse, France

[21] Appl. No.: 159,595

[22] PCT Filed: May 27, 1987

[86] PCT No.: PCT/FR87/00185
§ 371 Date: Jan. 27, 1988
§ 102(e) Date: Jan. 27, 1988

[87] PCT Pub. No.: WO87/07152
PCT Pub. Date: Dec. 3, 1987

[30] Foreign Application Priority Data
May 29, 1986 [FR] France ................................. 86 07856

[51] Int. Cl.$^4$ .............................................. A61L 9/01
[52] U.S. Cl. ...................................... 424/76.1; 424/405
[58] Field of Search ..................... 424/76.1, 5; 252/95

[56] References Cited

U.S. PATENT DOCUMENTS

| | | | |
|---|---|---|---|
| 4,078,050 | 3/1978 | Hart | 424/76.1 |
| 4,230,478 | 10/1980 | Zumbrunn | 252/95 |
| 4,294,821 | 1/1981 | Neumiller | 424/76.1 |
| 4,469,848 | 9/1984 | Hooper et al. | 424/78 X |
| 4,599,677 | 4/1986 | Hooper et al. | 252/95 |

FOREIGN PATENT DOCUMENTS

| | | |
|---|---|---|
| 0005618 | 5/1979 | European Pat. Off. |
| 458192 | 3/1928 | Fed. Rep. of Germany |
| 1590898 | 5/1970 | France |
| 2416016 | 2/1978 | France |

Primary Examiner—Thurman K. Page
Assistant Examiner—L. R. Horne
Attorney, Agent, or Firm—Browdy and Neimark

[57] ABSTRACT

The agent or agents of the invention, taken alone or as mixtures, belong to the family of compounds used in perfumery for their odoriferous properties presenting additionally a vapor tension lower or equal to 4 Pa at 25° C.

5 Claims, 2 Drawing Sheets

AGENT NEUTRALIZING BAD SMELLS FROM EXCRETIONS AND EXCREMENTS OF ANIMALS

The present invention concerns a means which effectively combats and neutralizes disagreeable odours from animal excretions and excrement.

It is known that it is very difficult to get rid of disagreeable odours due to animal excretions especially in the case of domestic animals, particularly cat urine and excrement, but also the odours from excretions from farm animals such as pigs, cattle, sheep, rabbits, poultry and other farmyard animals.

In the particular case of cat urine and excrement, their odour is particularly clinging and persistent. It turns out that whatever the perfuming or deodorising agent used to neutralize these disagreeable odours, these reappear after a certain time once the perfume's or deodorant's own odour has disappeared through evaporation. Indeed, in centres where animals such as pigs, cattle, sheep or rabbits are bred, the odours emanating from the pens or locations occupied by these animals are not, in general, dealt with due to a lack of effective means.

The present invention now provides a means having the effect of either preventing development of an odour after an animal has discharged or deposited its excretions or excrement on its litter, manure gulley or any other surface, i.e. as a preventive measure, or effectively combatting by neutralizing disagreeable odours which have already developed either on a surface or at a location following deposition by domestic or farm animals of excretions or excrement or accumulation of these excretions or excrement.

Accordingly, the present invention covers compounds having its effect and characterised by the fact that they belong to the family of compounds usually used in perfumery for their odoriferous properties but having, in addition, a vapour tension of less than or equal to 4 Pa at 25° C.

The invention also covers applications of these compounds as well as formulations containing at least one of these as will be made more clear from the following description.

In general, compounds selected from the following may generally be cited as falling within the scope of the invention:
- aliphatic alcohols, advantageously from $C_{10}$ to $C_{12}$, such as decanol, citronellol, geraniol;
- aldehydes, advantageously from $C_{10}$ to $C_{13}$, either aliphatics such as normal or branched dodecanal, myrac aldehyde or aromatics such as cyclamen aldehyde heliotropine, para-methylphenylacetaldehyde, vanillin and its derivatives;
- aliphatic ketones, advantageously $C_{13}$ and $C_{14}$, such as alpha and beta ionones and damascones as well as aliphatic and aromatic ketones having a musk-like odour and having up to 18 carbon atoms;
- aliphatic esters, advantageously from $C_8$ to $C_{15}$, such as methyl dihydrojasmonate, methyl jasmonate, methyl cinnamate, ethyl methylphenylglycidate, aromatic esters, such as methyl anthranilate, methyl N-methyl-anthranilate, p-cresyl phenylacetate, amyl salicylate;
- aromatic lactones, such as coumarin, dihydrocoumarin and aliphatic lactones, such as gamma-decalactone, dodecalactone and undecalactone;
- phenols, such as eugenol and isoeugenol;
- aromatic ethers, such as diphenyl oxide, methyl and ethyl ethers of naphthol, galaxolide;
- nitro compounds of the amine type, such as indole and its reaction products with hydroxycitronellal termed indolene, and aliphatic nitriles, such as tridecene-2-nitrile;
- aromatic amines including pyridinic derivatives, such as 2-(2'-methyl-pent-2'-enyl)-5-methylpyridine.

Among the compounds mentioned above, coumarin, allylionone, eugenol and iso-eugenol, methyl dihydrojasmonate, indole and indolene, helional, alpha- and beta-ionone and 2-(2'-methyl-pent-2-enyl)-5-methylpyridine are cited preferably.

Those compounds which are liquid may be used as they are. On the other hand, crystalline compounds are used following dissolution in their usual solvent, well known in perfumery, such as ethyl phthalate, benzyl benzoate, ethyl citrate and their analogues.

In addition, if desired the compounds according to the invention may also be used in combinations in variable proportions giving a formulation having practically no disagreeable olfactive effect.

There is, however, nothing to prevent augmenting the olfactive effect of the formulation for application on the user or environment by adding other primary perfuming substances to the compounds according to the invention, taken singly or in combination.

The following examples are given by way of illustration and in no way limit the type of formulations which may be prepared producing prevention or effective neutralization of disagreeable odours resulting from excrement and/or deposits and/or the accumulation of animal excretions. Of course, and conforming to the invention, active compounds such as eugenol, coumarin, allylionone, methyl dihydrojasmonate, indolene or helional which figure in the formulation examples given below may be used singly. The other ingredients serve either as odoriferating agents or as solvent such as ethyl phthalate, written as E.P.

EXAMPLE 1

Formulation I ($F_1$)

For 1 000 g of formulation, the following compounds were mixed together.
citral, 38 g
linalyl acetate, 114 g
citral diethylactal, 38 g
eugenol, 51 g
linalol, 228 g
hexenyl acetate, 10% in E.P., 51 g
E.P. q.s. to 1 000 g.

EXAMPLE 2

Formulation II ($F_2$)

As in example 1 the following compounds were mixed together (to make 1 000 g of formulation)
coumarin, 25 g
allylionone, 38 g
methyl dihydrojasmonate, 25 g
indolene, 25 g
4-(4-hydroxyphenyl)-2-butanone, 13 g
  1% in P.E.,
helional, 10 g
alpha-hexylcinnanic aldehyde, 253 g
E.P. q.s. to 1 000 g.

When applied in solution in an appropriate solvent, for example in a 6% dose, the compounds of the invention proved themselves to be particularly active both in preventing the development or release of disagreable odours expected when animals spread their excretions or deposit their excrement in locations which may be intended for such use, and in annihiliating, destroying or removing odours which had already developed in the same locations or even in other locations when, accidentally, these same animals rid themselves of these excretions or deposited their excrement.

In this way in particular, as a preventive measure, one or other of the above formulations $F_1$ or $F_2$ was sprayed on cat litter. Whether the spraying was repeated or not, it was established that the effect of each spraying was durable, that the treated litter had no repulsive effect on the animal and, consequently, the product constituting said litter, for example sawdust, perlite and analogues thereof could be economised upon. Neutralization of odours was practically complete, whence the disappearance of all resulting sources of annoyance. Similarly, carrying out similar spraying(s) of litter which was already soiled removed the disagreeable odours resulting from the deposition of excretions or excrement between litter changes.

EXAMPLE 3

The following experiments were carried out: commercial attapulgite used for cat litter was taken and washed several times with purified methylene chloride. After eliminating all residual solvent the attapulgite was considered to be ready for use.

After use by a given group of animals (castrated and uncastrated males, females), the attapulgite was strongly impregnated with the urine of these cats which was extracted using purified methylene chloride.

After elimination of the extraction solvent by distillation under normal pressure over a 150 cm long column filled with raschig packing a crude mixture of brown colour having a typical and extremely disagreeable odour was obtained.

Upon examination using gas phase chromatography on a 50 m long, 0.32 mm diameter, silicone SE 30 coated fused silica capillary column, this mixture was seen to be composed of numerous constituents (FIG. I). The depth of analytical examination was increased using coupled gas phase chromatography—mass spectrometry and coupled gas phase chromatography—infrared Fourier transform spectroscopy.

Olfactive examination of each constituent corresponding to each chromatographic peak, this time using a 30 m long, 0.53 mm diameter column having the same polarity, showed the presence of several very bad smelling constituents having sulphurated, foetid, smokey, sweaty, varied vegetable, etc type odours. In particular, constituent X, marked with an arrow on FIG. I, exhibited most of these properties to an extremely pronounced degree.

As in the preceding examples, a spray of formulation $F_3$ was used containing among others and particularly the following products: $\underline{E}$-citral, eugenol, coumarin and helional.

The treated litter, "visited" for a long period by the same animals as before, as well as a control litter impregnated in the same way with formulation $F_3$, but not soiled by the animals, was extracted with purified methylene chloride under the same conditions as before.

In each case a crude extract was obtained which was analysed using coupled gas phase chromatography-mass spectrometry.

The upper chromatogram in FIG. II corresponds to the crude extract from the litter impregnated with formulation $F_3$ but not soiled by urine; arrows 1, 2, 3 and 4 indicate the presence of $\underline{E}$-citral, eugenol, coumarin and helional respectively. The lower chromatogram corresponds to the crude extract from the litter impregnated with formulation $F_3$ and soiled with urine.

Under these conditions, the following significant phenomena were observed:

in the litter soiled with urine, peak X attributed to the very bad smelling substance completely disappeared;

concomitant disappearance of helional and a substantial diminution in the proportions of $\underline{E}$-citral, coumarin and particularly eugenol (these variations are not, however, limited to these products alone);

in addition, the extract from the liter which was soiled with urine did not have a particularly disagreeable odour.

In another respect, it is to be noted that in the case of an accident, i.e. if an animal were to soil other surfaces, smooth or not, such as metallic surfaces, fabrics, carpets, cushions or the like, the said formulation spray(s) would completely remove any disagreeable odour which persisted following cleaning of said surfaces.

One other interesting application of the agents according to the invention lies in the veterinary field. It has been established that, despite all precautions and means used currently either to disinfect or attempt to deodorise working surfaces in veterinary surgeries, an animal coming into a consulting room is sensitive to residual odours left by the preceding animal treated in the consulting room.

Veterinary surgeons know very well that a dog, when it comes into the surgery, probably out of fear, secretes a very strong smelling, disagreeable substance from its anal glands, said substances being very difficult to neutralize.

Now the products according to the invention, when sprayed as a preventive measure on the anal and perianal regions of dogs, totally neutralise the effect resulting from this secretion from the glands in question. Similarly, worktops and examination areas in veterinary surgeries, whether metallic or not, when sprayed with the products according to the invention, are totally freed of disagreeable effects due to these animal odours whether the odour is due to excretions or to simple physical contact with the examination surfaces.

It has also been established that the products according to the invention are also effective when sprayed on other animal litters such as pigs' manure gulleys, rabbit or sheep litters, pens, farmyards, birdcages, aviaries, etc.

As indicated above, these products may be used singly or in combination with each other and/or with other odoriferous agents according to the results desired to improve an ambient atmosphere. These products, singly or in combination, may be used simply in their solvent if the products are in the solid state or with solvents facilitating their application or homogeneity. The proportions themselves are variable according to the situation and the intensity of the odour to be combatted.

It goes without saying that the present invention has been described by way of non-limiting explanation only. Any modification, particularly as regards technical equivalents, may be made without departing from the scope of the invention.

We claim:

1. A method for neutralizing disagreeable odours from animal excretions and excrement, comprising the steps of applying to a surface having a significant odour from animal excretions or excrement an agent including a compound selected from the group consisting of $C_{10}$ to $C_{12}$ aliphatic alcohols, $C_{10}$ to $C_{13}$ aldehydes, $C_{13}$ to $C_{18}$ aliphatic ketones, aromatic ketones having a musk odour and up to 18 carbon atoms, $C_8$ to $C_{15}$ aliphatic esters, methyl anthranilate, methyl N-methylanthranilate, p-cresyl phenylacetate, amyl salicylate, coumarin, dihydrocoumarin, gammadecalactone, dodecalactone, undecalactone, eugenol, isoeugenol, diphenyl oxide, the methyl and ethyl ethers of naphthol, galaxolide, indole and its reaction products with hydroxycitronella, tridecene-2-nitrile, and 2-(2'-methyl-pent-2'-enyl)-5-methyl pyridine, in an amount effective to neutralize disagreeable odors from said excretions or excrement, said agent having a vapour tension of less than or equal to 4 Pa at 25° C.

2. The method according to claim 1, wherein said agent is selected from the group consisting of coumarin, allylionone, eugenol, isoeugenol, methyl dihydrojasmonate, indole, indolene, helional, alpha-ionene, beta-ionone and 2-(2'-methyl-pent-2'-enyl)-5-methylpyridine.

3. The method of claim 1, wherein said aliphatic alcohol is selected from the group consisting of decanol citronellol and geraniol, said aldehyde is selected from the group consisting of dodecanal, myrac aldehyde, cyclamen aldehyde, helional, heliotropine, paramethylphenylacetaldehyde, and vanillan, said aliphatic ketones are selected from the group consisting of alpha and beta ionones and damascones, and said aliphatic esters are selected from the group consisting of methyl dihydrojasmonate, methyl jasmonate, methyl cinnamate and methylphenylglycidate.

4. The method of claim 1, wherein said surface is a veterinary worktop or cat litter.

5. An agent for the neutralization of disagreeable odors from animal excrement comprising a mixture of E-citral, eugenol, coumarin and helional.

* * * * *